United States Patent

Pan et al.

[11] Patent Number: 5,808,068
[45] Date of Patent: Sep. 15, 1998

[54] HIV NUCLEAR LOCALIZATION INHIBITORS

[75] Inventors: Senliang Pan, Flushing; Michael Bukrinsky, Glenwood Landing, both of N.Y.; Omar K. Haffar, Seattle, Wash.

[73] Assignee: The Picower Institute for Medical Research, Manhasset, N.Y.

[21] Appl. No.: 912,076

[22] Filed: Aug. 15, 1997

[51] Int. Cl.[6] .................... C07D 239/24; A61K 31/495
[52] U.S. Cl. .................... 544/315; 544/298; 514/269; 514/274
[58] Field of Search .................... 544/315, 298; 514/269, 274

[56] References Cited

FOREIGN PATENT DOCUMENTS 06073022  3/1994  Japan .

OTHER PUBLICATIONS

Popov et al., Proc. Natl. Acad. Sci. USA, vol. 93, pp. 11859–11864, 1996.

Dubrovsky et al., Molcular Medicine, vol. 1, No. 2, pp. 217230, 1995.

Primary Examiner—José G. Dees
Assistant Examiner—Sabiha N. Qazi
Attorney, Agent, or Firm—Jeffrey B. Oster

[57] ABSTRACT

There is disclosed a genus of compounds that have anti-HIV infection therapeutic activity and inhibit nuclear localization of the HIV preintegration complex.

11 Claims, 4 Drawing Sheets

HIV NUCLEAR LOCALIZATION INHIBITORS

TECHNICAL FIELD OF THE INVENTION

The present invention provides a genus of compounds that have anti-HIV anti-infective therapeutic activity and that inhibit nuclear localization of the HIV preintegration complex.

BACKGROUND OF THE INVENTION

In the past decade, infection with the human immunodeficiency virus-type 1 (HIV-1) has reached pandemic proportions. In addition to the overwhelming increase in the number of people infected with HIV-1 in sub-Saharan Africa, there has been a significant increase in new infections in Europe and North America. Of equal concern is the emergence of HIV-1 in southeast Asian countries such as Thailand and Malaysia. Based on the current rate of infection, it is estimated that southeast Asia may, in the near future, surpass Africa as the hot spot of the world. Therefore, infection with HIV-1 and development of AIDS proceeds unabated. In the absence of a protective vaccine, post-infection therapy is the only management tool available to health care providers.

The identification of long term non-progressors strongly suggested that therapy for HIV-1 infection may delay the onset of disease following infection. To date, the principle targets for HIV-1 therapy have been the viral enzymes, reverse transcriptase (RT) and protease, that are important for the virus life cycle. Inhibitors of either of these enzymes successfully reduced the virus load in patients, resulted in increased $CD4^+$ T lymphocyte subsets and have become commercially available drugs for HIV infection treatment. Both of these end points have been shown to be good correlates for positive prognosis. Importantly, combination therapies utilizing RT inhibitors together with protease inhibitors in a variety of regimens resulted in reduction of the circulating virus in the blood to below detectable levels. These clinical results showed that maintenance therapy for HIV-1 infection and AIDS is achievable.

However, emergence of virus isolates resistant to the applied anti-viral drugs, as well as cross resistance to multiple drugs within a class of inhibitors is predicted to limit the application of combination therapy. These results strongly indicated the need for continued novel drug development, and continued identification of novel targets, other than the virus enzymes.

Human immunodeficiency virus type-1 and other lentiviruses infect non-dividing terminally differentiated cells such as primary macrophages (Gendelman et al., J. Virol. 58:67–74, 1986; , Gartner et al., Science 233:215–219, 1986), primary blood dendritic cells (Langhoff et al., Proc. Natl. Acad. Sci. USA 88:998–8002, 1991), and epidermal Langerhan's cells (Ramazzotti et al., Immunology 85:94–98, 1995). This is facilitated by the active importation of the HIV-1 preintegration complex (PIC), which incorporates the viral genome, across the intact nuclear envelope of the non-dividing cell (Bukrinsky et al., Proc. Natl. Acad. Sci. USA 89:6580–6584, 1992; Bukrinsky et al., Nature 365:666–669, 1993; and von Schwedler et al., Proc. Natl. Acad. Sci. USA 91:6992–6996, 1994). In addition, HIV-1 can establish productive infection in activated primary T cells at all steps of the cell cycle, prior to and including the M phase, when dissolution of the nuclear envelope occurs. Thus, active nuclear importation obviates the requirement for cell division, thus allowing HIV-1 to infect non-proliferating as well as proliferating cells (Lewis et al., EMBO J. 11:3053–3058, 1992), the usual targets of retroviruses (Roe et al., EMBO J. 12:2099–2108, 1993; and Lewis and Emerman, J. Virol. 68:510–516, 1994).

In addition to the viral genomic RNA, the PIC is composed of the gag-derived matrix antigenprotein (MA), nucleocapsid protein (NC), reverse transcriptase (RT), integrase (IN), and viral protein "r" (vpr). Reverse transcription and production of the nascent cDNA is completed in context of the PIC in the cytoplasm of the infected target cell, prior to nuclear entry. It was recently shown (Gallay et al.,J. Virol. 70:1027–1032, 1996; and Popov et al., Proc. Natl. Acad. Sci. USA 93:11859–11864, 1996) that the PIC of HIV-1 associates with karyopherins, the cellular proteins involved in active nuclear importation (reviewed in Adam, Trends Cell Biol. 5:189–191, 1995). Karyopherin α binds to target proteins via their nuclear localization sequence (NLS), while karyopherin β mediates docking of the karyopherin α-target protein complex to nuclear pore structures (Radu et al.,Proc. Natl. Acad. Sci. USA 92:1769–1773, 1995; Moroianu et al., Proc. Natl. Acad. Sci USA 92:2008–2011, 1995; Görlich et al., Nature (London) 377:246–248, 1995; Adam and Gerace, Cell 66:837–847, 1991; Görlich and Mattaj, Science 271:1513–1518, 1996; and Hurt, Cell 84:509–515, 1996).

HIV-1 matrix antigen protein contains one defined ($K^{26}KKYK$) and one putative ($K^{110}SKKK$) NLS, and represents a major karyophilic structure within the PIC (Bukrinsky et al., Nature 365:666–669, 1993; von Schwedler et al.,Proc. Natl. Acad. Sci. USA 91:6992–6996, 1994; Gallay et al., J. Virol. 70:1027–1032, 1996; and Bukrinsky et al. Proc. Natl. Acad. Sci. USA 90:6125–6129, 1993). Synthetic peptides encompassing either of the two MA NLS bound both identified human karyopherin a present in B cell and T cell lysates (Nadler et al., J. Biol. Chem. 272, 4310–4315, 1997). Mutations in the KKKYK NLS of MA, alone or in combination with the deletion of Vpr, reduced nuclear importation of the HIV-1 PIC and inhibited infection of primary macrophage cultures (von Schwedler et al.,Proc. Natl. Acad. Sci. USA 91:6992–6996, 1994; Heizinger et al., Proc. Natl. Acad. Sci. USA 91:7311–7315, 1992), as well as growth-arrested T cells (Bukrinsky et al., Nature 365:666–669, 1993) and $CD4^+$-HeLa cell cultures (Emerman et al., Nature (London) 369:107–108, 1994). Single amino acid substitutions within the KKKYK NLS also reduced binding of the HIV-1 PIC to yeast karyopherin α in vitro (Popov et al., Proc. Natl. Acad. Sci. USA 93:11859–11864, 1996), thus providing a link between binding of PIC to karyopherin α, nuclear import, and viral replication in non-dividing cells.

SUMMARY OF THE INVENTION

The present invention provides a compound having the formula I:

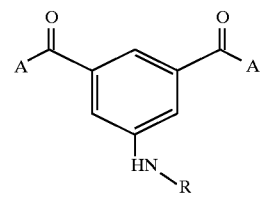

-continued

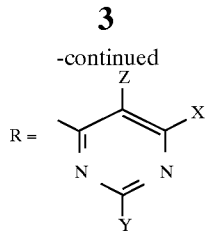

wherein A is independently a straight or branched $C_{1-6}$ alkyl, a straight or branched $C_{2-6}$ alkenyl or a $C_{1-6}$ alkoxy; Y is —S—A wherein A is independently defined above; and Z and X are independently H, —$(CH_2)_n$—$NH_2$ wherein n is an integer from 0 to 6, a straight or branched $C_{1-6}$ alkyl, a straight or branched $C_{2-6}$ alkenyl or a $C_{1-6}$ alkoxy. Preferably, A is methyl, X is —$NH_2$ and Z is H or amino. The present invention further provides a pharmaceutical composition comprising a compound from formula I in a pharmaceutically acceptable carrier.

The invention further provides a process for synthesizing a compound of formula I, comprising the steps of:

(a) providing a solution of acetyl chloride in a short chain alcohol;

(b) adding to the solution a substituted 6-halogen-methylmercaptopyrimidine and a 3,5-dialkylaniline to form a mixture;

(c) refluxing the mixture to join the aniline derivative to the 6 position of the pyrimidine derivative; and (d) drying the mixture to obtain a solid final product according to formula I.

Preferably, the substituted 6-halogen-methylmercaptopyrimidine is 4-amino-6-chloro-2-methylmercaptopyrimidine and the 3,5-dialkylaniline is 3,5-diacetylaniline.

BRIEF DESCRIPTION OF THE DRAWINGS

FIG. 4 shows a dose-response relationship for compound 62 ("CNI-H6297") under the foregoing experimental conditions in this predictive assay of HIV anti-infective properties.

DETAILED DESCRIPTION OF THE INVENTION

Figure 1:
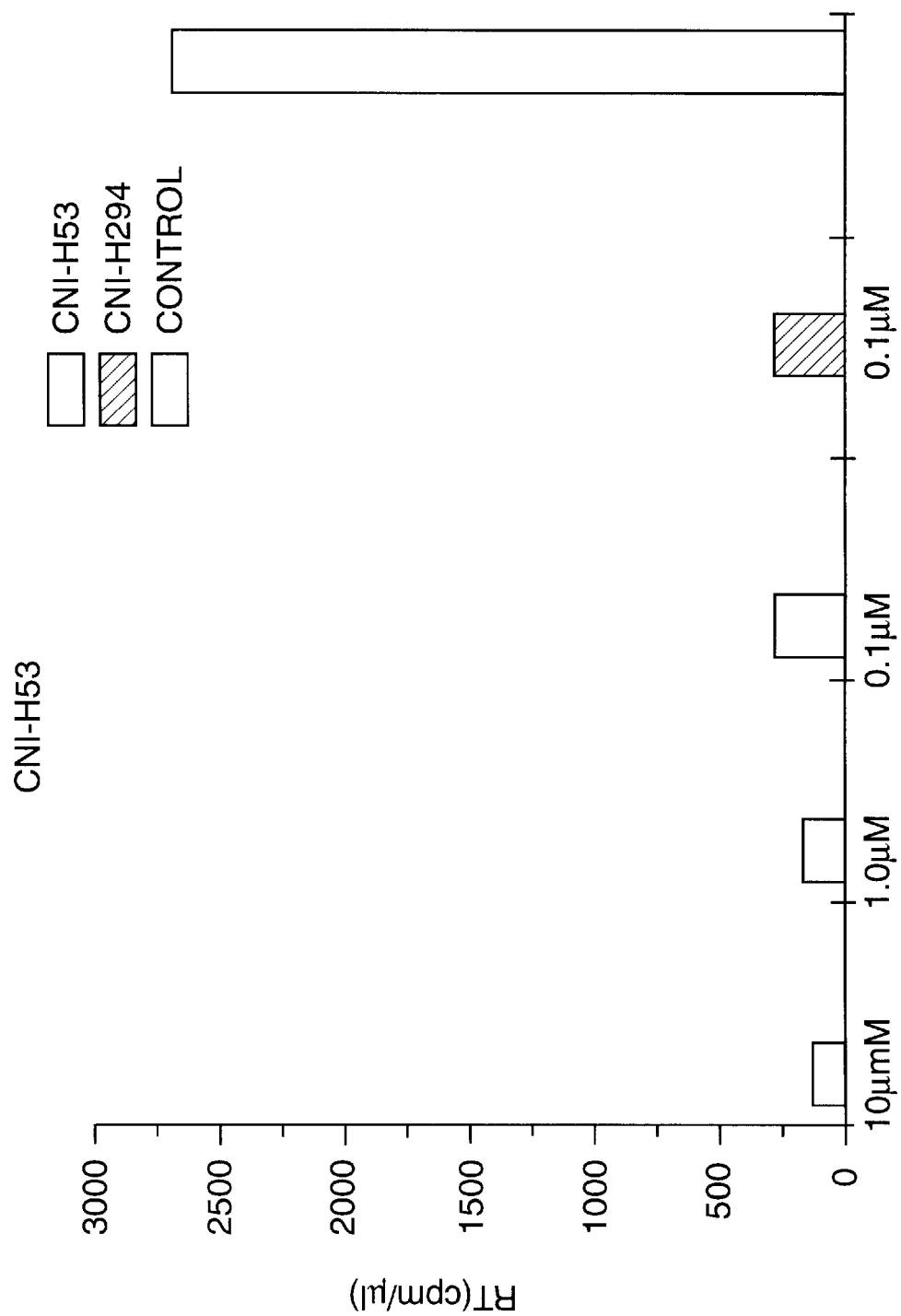
FIG. 1 shows a graph comparing, in an assay of anti-HIV activity in macrophage cultures, anti-HIV therapeutic activity of inventive compound 53 with a structurally similar compound ("cni-h0294") that differs from compound 53 of the present invention by having a positive charge in the pyrimidine moiety and lacking a stipulated sulfur group substituted to the pyrimidine moiety. The assay measures reverse transcriptase activity in the infected macrophage culture supernatants as a measure of virus production. These data can be directly correlated to efficacy treating HIV infection. These data show that inventive compound 53 was more efficacious that structurally similar compound 2.

The present invention provides a compound having the formula I:

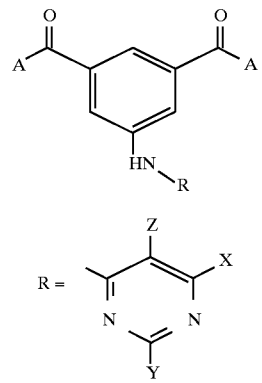

wherein A is independently a straight or branched $C_{1-6}$ alkyl, a straight or branched $C_{2-6}$ alkenyl or a $C_{1-6}$ alkoxy; Y is —S—A wherein A is independently defined above; and Z and X are independently H, —$(CH_2)_n$—$NH_2$ wherein n is an integer from 0 to 6, a straight or branched $C_{1-6}$ alkyl, a straight or branched $C_{2-6}$ alkenyl or a $C_{1-6}$ alkoxy. Preferably, A is methyl, X is —$NH_2$ and Z is H or amino. The present invention further provides a pharmaceutical composition comprising a compound from formula I in a pharmaceutically acceptable carrier.

The invention further provides a process for synthesizing a compound of formula I, comprising the steps of:

(a) providing a solution of acetyl chloride in a short chain alcohol;

(b) adding to the solution a substituted 6-halogen-methylmercaptopyrimidine and a 3,5-dialkylaniline to form a mixture;

(c) refluxing the mixture to join the aniline derivative to the 6 position of the pyrimidine derivative; and (d) drying the mixture to obtain a solid final product according to formula I.

Preferably, the substituted 6-halogen-methylmercaptopyrimidine is 4-amino-6-chloro-2-methylmercaptopyrimidine and the 3,5-dialkylaniline is 3,5-diacetylaniline.

The present invention provides an improvement in the design of small organic molecules that are effective for inhibiting HIV infection by creating an integral sulfur-containing substituent (see "Y" in formula I). The presence of this substituent, not disclosed or suggested in alternative HIV inhibitors, has provided compound characteristics of improved cellular absorption and, as a result, improved potency not disclosed or suggested by the structures of the alternative HIV preintegration complex inhibitors.

The inventive compounds were active to inhibit receptor-mediated nuclear importation in the infection of peripheral blood mononuclear cell (PBMC) cultures. The compound, CNI-H0294, is thought to interact with the HIV-1 PIC (preintegration complex) by forming partial Schiff bases with adjacent lysine residues in the MA NLS (Popov et al., *Proc. Natl. Acad. Sci.* USA 93:11859–11864, 1996; Dubrovsky et al., *Molec. Med.* 1:217–230, 1995), contains a positive charge in its substituted pyrimidine moiety that may serve to limit its cellular bioavailability and it oral absorption characteristics. It has been previously shown that CNI-H0294 interferes with the association of the HIV PIC with the yeast karyopherin a (Popov et al., *Proc. Natl. Acad. Sci.* USA 93:11859–11864, 1996), and effectively inhibits infection of primary macrophage cultures with the macrophage tropic isolate $HIV_{ADA}$ ($IC_{50}$=10 nM–50 nM) (Dubrovsky et al., *Molec. Med.* 1:217–230, 1995).

It should be noted that in order for a therapeutic agent to be effective as a PIC inhibitor, it must act intracellularly. Thus, potency is directly related to cellular bioavailability. Moreover, the preferred route of administration to treat HIV infection on a chronic basis is oral to increase patient compliance. Therefore, it is highly desirable to have a HIV anti-infective compound be administered orally and have high oral bioavailability.

Compound Synthesis

The exemplary compound, 2-methylmercapto-4-amino-6-(3',5'-diacetylphenyl)aminopyrimidine (compound 53) was synthesized. There are two methods for synthesizing compound 53. The first method starts by adding acetyl chloride (0.8 ml, 11 mmol) to 60 ml absolute ethanol. The mixture was stirred for 15 minutes to form a hydrochloric ethanol solution. Then, 1.75 g (10 mmol) of 4-amino-6-chloro-2-methylmercaptopyrimidine (Aldrich) and 3,5-diacetylaniline (1.8 g, 10 mmol) (Aldrich) were added in sequence. The reaction mixture was refluxed for 24 hours and eventually turned a brown color. The ethanol was evaporated to dryness and 20 ml $CHCl_3$ was added to the residue (a gray solid residue).and separated. The gray solid was filtered to give 1.7 g crude product after drying. A TLC (thin layer chromatography analysis showed that the unreacted starting material stayed in the $CHCl_3$ layer. Approximately 0.5 g of crude product was recrystalized in methanol to give 370 mg of analytical pure sample (yield 39.8%).

There is a second method to product compound 53. Specifically, HCl (90 $\mu$l) was added to a mixture containing 4-amino-6-chloro-2-methylmercapto pyridine (1 mmol) and 3,5-diacetylanaline in 5 ml $H_2O$ (1.1 mmol). The reaction mixture was heated at 90°–100° C. for 1 hour, and then cooled down in an ice bath. Two ml of 1N KOH was added to neutralize the acid. The mixture was stirred for 10 minutes, a precipitate formed and then the precipitate was filtered out to give 285 mg dry, pale brown crude product (yield 90%). A TLC analysis (MeOH:$CH_2Cl_2$=10:0.6) showed only one spot for a pure product. Recrystalization from a methoxyethanol solution provided 267 mg of analytically pure product (yield 84.5%). The recrystalized product was dried under vacuum (78° C.) with a melting point of 264.8° C.–268.6° C.

The analytical specifications of compound 53 are molecular weight 316.4 and $C_{15}H_{16}N_4O_2S$. Additionally, $^1$HNMR (DMSO-$d_6$, 270 MHz): δ 2.46 (s, 3H, SMe), 2.6 (s,6H, 2 $COCH_3$), 5.52 (s, 1H, $C_5$—H), 6.52 (br s, 2H, $NH_2$), 8.01 (s, 1H, Ar—H), 8.45 (s, 2H, Ar—H), 9.41 (s, 1H, NH). Further analysis of the final product compared the found elemental analysis versus the calculated elemental analysis:

Calculated: C56.94 H5.10 N17.17 S10.14 Found: C56.84 H4.99 N17.55 S10.18

Illustrative compound 62 was synthesized by mixing 803 mg (5 mmol) 2-methylmercapto-4-chloropyrimidine and 886 mg (5 mmol) 3,5-diacetylaniline in 20 ml of water. In addition, 0.42 ml concentrated HCl was added. This reaction mixture was heated at 90°–100° C. for 4 hours, and then cooled down in an ice bath. The cooled mixture had 5 ml of 1N KOH added to neutralize the acid pH from the HCl. The mixture was stirred for 10 minutes in an ice bath to form a precipitate. The precipitate was filtered out to give 1.44 g dry pale brown crude product. A thin layer chromatography (TLC) analysis in methanol:$CH_2Cl_2$ (1:25) showed only one spot. The crude precipitate was recrystalized from methoxyethanol and dried under vacuum to give 1.42 grams of pure 2-methylmercapto-4-(3',5'-diacetylphenyl) aminopyrimidine (compound 62) with an overall yield of 94%. The NMR analysis found the formula $C_{15}H_{15}N_3O_2S$ with a molecular weight of 301.38.

calculated: C 59.78 H 5.02N 13.94 S 10.64 found: C 59.32 H 4.80N 13.81 S 10.34

Pharmaceutical Formulation

The inventive pharmaceutical complex or inventive pharmaceutical combination can be administered to a patient either by itself (complex or combination) or in pharmaceutical compositions where it is mixed with suitable carriers and excipients. The inventive compound or pharmaceutical composition can be administered parenterally, such as by intravenous injection or infusion, intraperitoneal injection, subcutaneous injection, or intramuscular injection. The inventive compound or pharmaceutical composition can be administered orally or rectally through appropriate formulation with carriers and excipients to form tablets, pills, capsules, liquids, gels, syrups, slurries, suspensions and the like. The inventive compound or pharmaceutical composition can be administered topically, such as by skin patch, to achieve consistent systemic levels of active agent. The inventive compound or pharmaceutical composition is formulated into topical creams, skin or mucosal patches, liquids or gels suitable to topical application to skin or mucosal membrane surfaces. The inventive compound or pharmaceutical composition can be administered by inhaler to the respiratory tract for local or systemic treatment of HIV infection.

The dosage of the inventive compound or pharmaceutical composition suitable for use with the present invention can be determined by those skilled in the art from this disclosure. The pharmaceutical composition will contain an effective dosage (depending upon the route of administration and pharmacokinetics of the active agent) of the inventive compound or pharmaceutical composition and suitable pharmaceutical carriers and excipients, which are suitable for the particular route of administration of the formulation (i.e., oral, parenteral, topical or by inhalation). The active compound is mixed into the pharmaceutical formulation by means of mixing, dissolving, granulating, dragee-making, emulsifying, encapsulating, entrapping or lyophilizing processes. The pharmaceutical formulations for parenteral administration include aqueous solutions of the active complex or combination in water-soluble form. Additionally, suspensions of the active compound may be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. The suspension may optionally contain stabilizers or agents to increase the solubility of the complex or combination to allow for more concentrated solutions.

Pharmaceutical formulations for oral administration can be obtained by combining the active compound with solid excipients, such as sugars (e.g., lactose, sucrose, mannitol or sorbitol), cellulose preparations (e.g., starch, methyl cellulose, hydroxypropylmethyl cellulose, and sodium carboxymethyl cellulose), gelatin, gums, or polyvinylpyrrolidone. In addition, a desintegrating agent may be added, and a stabilizer may be added.

EXAMPLE 1

This example illustrates several in vitro experiments in predictive models of treatment of HIV infection to show the therapeutic utility of the inventive compounds. Macrophages, isolated and purified as described by Schumandtmanesalla et al. (Virology, 1997)) were infected with HIV-1 at a multiplicity adjusted according to p24 content (10 ng p24 per $10^6$ cells). Compound (53 in FIG. 1 or 62 in FIG. 2) was added at different concentrations. In addition, positive control compound (called "CNI-H294" in FIG. 1 and "cni-h0294" in FIG. 2) was added at the concentration indicated. After a two hour incubation for viral adsorption, excess viruses were washed away, and the cells were incubated for additional indicated periods prior to analysis. RT, or reverse transcriptase activity, was measured by standard techniques in 7–11 days.

FIG. 1 shows a graph comparing anti-HIV therapeutic activity of inventive compound 53 with a structurally similar compound ("compound 2") having a positive charge in the pyrimidine moiety and lacking a required sulfur group substituted to the pyrimidine moiety in an assay of anti-HIV activity in H9 cell cultures. The assay measures reverse transcriptase activity in the infected macrophage culture supernatants as a measure of virus production. These data can be directly correlated to efficacy treating HIV infection. These data show that inventive compound 53 was more efficacious that structurally similar compound 2.

Figure 2:
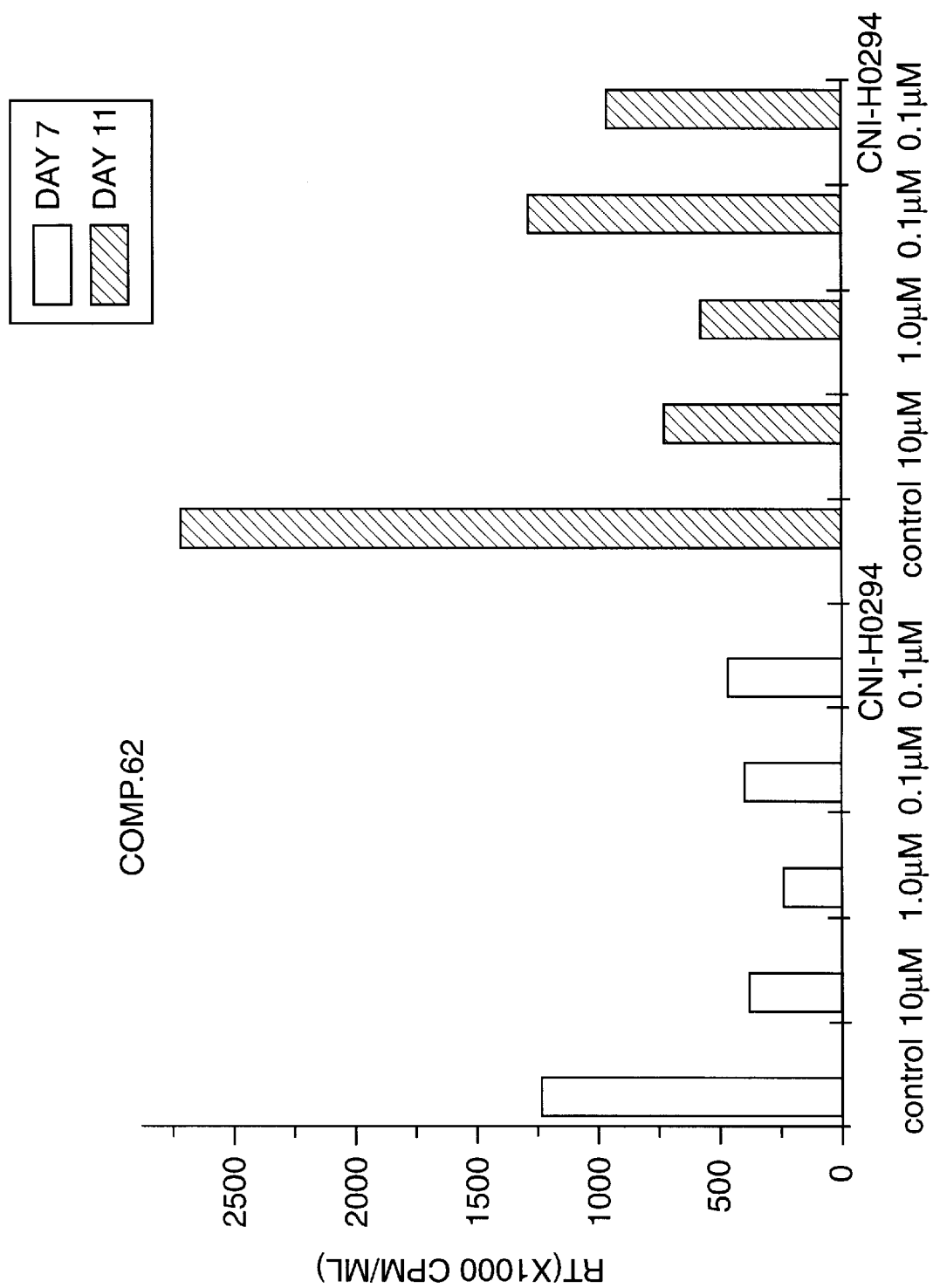
FIG. 2 shows a graph comparing anti-HIV therapeutic activity, in an assay of anti-HIV activity in macrophage cultures, of inventive compound 62 with a structurally similar compound ("cni-h0294") that differs from compound 62 of the present invention by having a positive charge in the pyrimidine moiety and lacking a stipulated sulfur group substituted to the pyrimidine moiety. The assay measures reverse transcriptase activity in the infected macrophage culture supernatants as a measure of virus production. These data can be directly correlated to efficacy treating HIV infection. These data show that inventive compound 62 was efficacious as an anti-HIV anti-infective agent.

FIG. 2 shows a graph comparing anti-HIV therapeutic activity of inventive compound 62 with a structurally similar compound ("cni-h0294") having a positive charge in the pyrimidine moiety and lacking a required sulfur group substituted to the pyrimidine moiety in an assay of anti-HIV activity in macrophage cultures. The assay measures reverse transcriptase activity in the infected H9 cell culture supernatants as a measure of virus production. These data can be directly correlated to efficacy treating HIV infection. These data show that inventive compound 62 was efficacious as an anti-HIV anti-infective agent.

EXAMPLE 2

Figure 3:
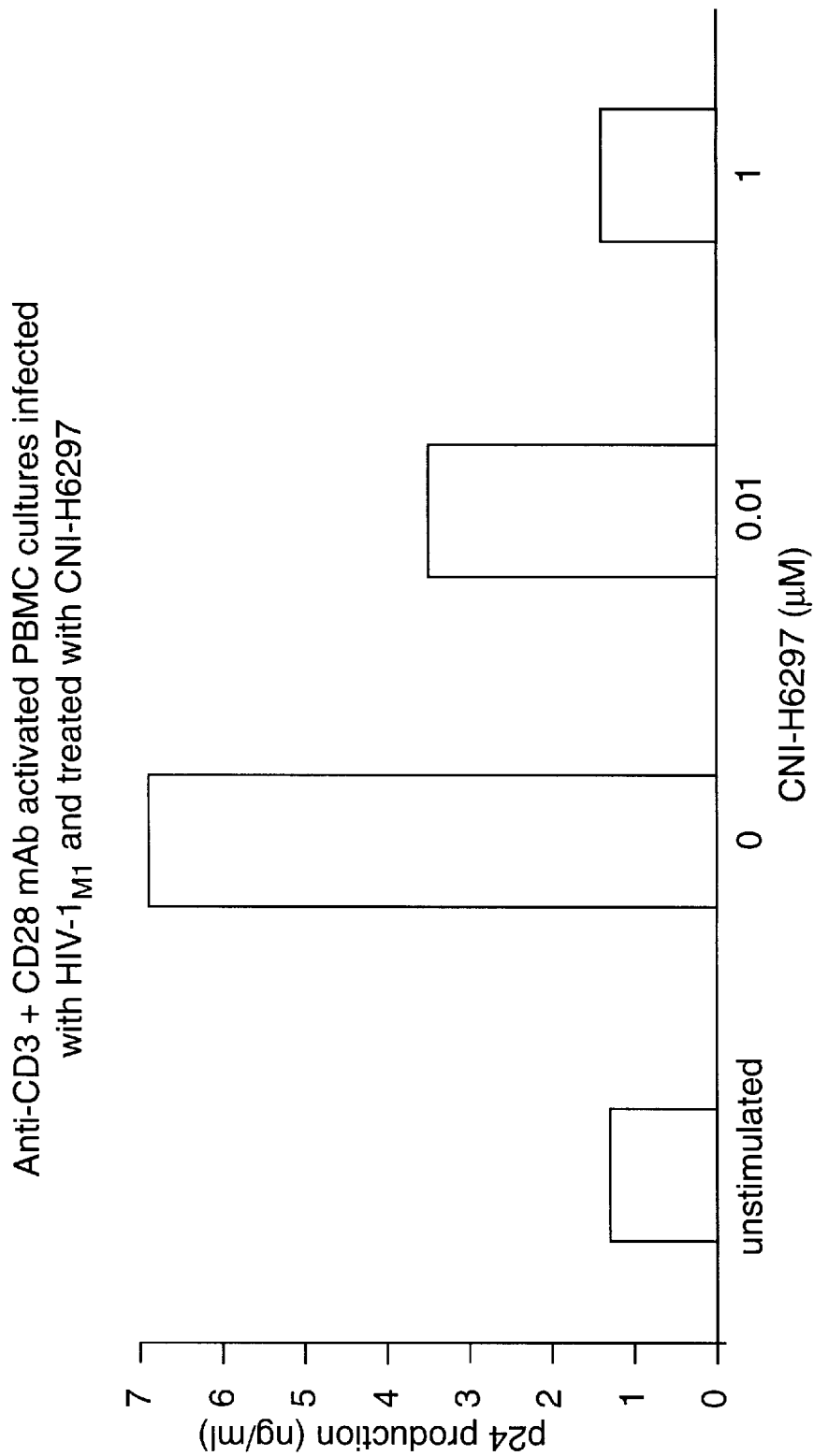
FIG. 3 shows a further analysis of therapeutic efficacy of compound 62 in activated (anti-CD3 and anti-CD28 monoclonal antibodies) peripheral blood mononuclear cell (PBMC) cultures infected with HIV-1 virus and treated with different concentrations of compound 62 ($\mu$M). The assay measures p24 as an index of viral replication and can be directly correlated to efficacy in treating HIV infection. These data show anti-viral efficacy of compound 62 in a dose-response fashion.

This example illustrates that compound 62 inhibits HIV-1 virus replication in acutely infected PBMC cultures activated with anti-CD3 and anti-CD28 monoclonal antibodies (FIG. 3). Peripheral blood mononuclear cells were isolated from an uninfected individual and depleted of CD8+ T lymphocytes using a CD8-specific monoclonal antibody, according to the procedure described by Smithgall et al., *J. Immunol.* 156:2324–2330, 1996. Briefly, the procedure substitutes separation with magnetic beads for complement-mediated lysis of antibody-bound cells. The remaining PBMC fractions were suspended in RPMI culture medium supplemented with 10% heat-inactivated human serum at $2\times10^6$ cells/200 μl. Cells were activated with anti-CD3 mAb (1 μg/ml) together with anti-CD28 mAb (1 μg/ml) in the presence of various concentrations of compound 62. This form of cell activation specifically targets CD3+ T lymphocytes in the population.

Cells were pretreated with antibody and test compound for 2–3 hours prior to addition of the virus inoculum. The virus used in this experiment, HIV-$1_{M1}$, is a patient-derived isolate, and was used at an approximate multiplicity of infection (MOI)=5 $TCID_{50}$. After 2 hr incubation for adsorption of virus, the cells were washed free of the inoculum, and then resuspended in 200 ml of culture medium supplemented with anti-CD3 and anti-CD28 mAbs together with varyious concentrations of compound 62 (to show a dose-response relationship). Cells were then placed into a U-bottom 96 well culture plate in 4–6 replicates at $1.5\times10^5$ cells/well. Virus production was measured on day 6–10 following infection using p24 production as an end point. The p24 antigen capture assay was performed according to the manufacturer's recommendations.

The data presented in FIG. 3 show a dose-response relationship at 0, 0.01 μM and 1.0 μM concentrations of compound 62 ("CNI-H6297") when using p24 as a measure of virus concentration.

Figure 4:
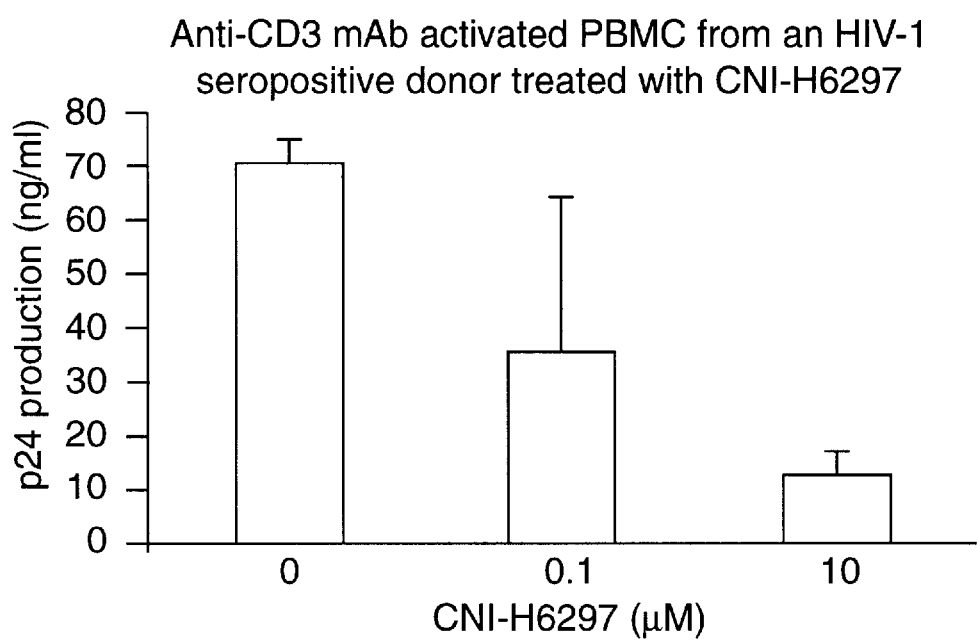
FIG. 4 shows that compound 62 also inhibited virus replication in PBMC from a HIV-1 infected individual when the PBMCs were activated in vitro with anti-CD3 mAb. PBMCs from a seropositive individual were collected and depleted of $CD8^+$ T lymphocytes as described above. Cells were suspended in culture medium and activated with anti-CD3 mAb (1 $\mu$g/ml). After 6–10 days virus production was evaluated by measuring levels of p24 in the culture supernatants and comparing treated to untreated cultures.

Compound 62 also inhibited virus replication in PBMC from a HIV-1 infected individual when the PBMCs were activated in vitro with anti-CD3 mAb. PBMCs from a seropositive individual were collected and depleted of CD8+ T lymphocytes as described above. Cells were suspended in culture medium and activated with anti-CD3 mAb (1 μg/ml). After 6–10 days virus production was evaluated by measuring levels of p24 in the culture supernatants and comparing treated to untreated cultures. FIG. 4 shows a dose-response relationship for compound 62 ("CNI-H6297") under the foregoing experimental conditions in this predictive assay of HIV anti-infective properties.

We claim:

1. A compound having the formula I:

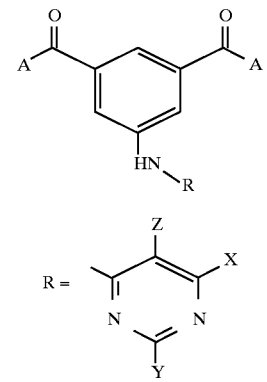

wherein A is independently a straight or branched $C_{1-6}$ alkyl, a straight or branched $C_{2-6}$ alkenyl or a $C_{1-6}$ alkoxy; Y is —S—A wherein A is independently defined above; and Z and X are independently H, —(CH$_2$)$_n$—NH$_2$ wherein n is an integer from 0 to 6, a straight or branched C$_{1-6}$ alkyl, a straight or branched C$_{2-6}$ alkenyl or a C$_{1-6}$ alkoxy.

2. The compound of claim 1 wherein A is methyl, X is —NH$_2$ and Z is H.

3. The compound of claim 1 wherein A is methyl, X is —NH$_2$ and Z is amino.

4. A pharmaceutical composition comprising a compound from claim 1 in a pharmaceutically acceptable carrier.

5. The pharmaceutical composition of claim 4 wherein A is methyl, X is —NH$_2$ and Z is H.

6. The pharmaceutical composition of claim 4 wherein A is methyl, X is —NH$_2$ and Z is amino.

7. A process for synthesizing a compound of formula I, comprising the steps of:

(a) providing a solution of acetyl chloride in a short chain alcohol;

(b) adding to the solution a substituted halogen-methylmercaptopyrimidine and a 3,5-dialkylaniline to form a mixture;

(c) refluxing the mixture to join the aniline derivative to the pyrimidine derivative; and (d) drying the mixture to obtain a solid final product according to formula I.

8. The process of claim 7 wherein the substituted 6-halogen-methylmercaptopyrimidine is 4-amino-6-chloro-2-methylmercaptopyrimidine and the 3,5-dialkylaniline is 3,5-diacetylaniline.

9. A method for treating HIV infection, comprising administering an effective amount of a compound having the formula I:

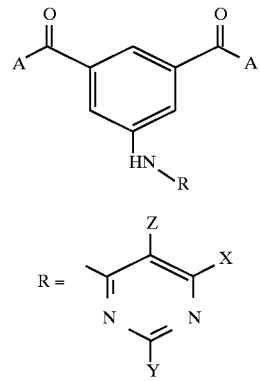

wherein A is independently a straight or branched C$_{1-6}$ alkyl, a straight or branched C$_{2-6}$ alkenyl or a C$_{1-6}$ alkoxy; Y is —S—A wherein A is independently defined above; and Z and X are independently H, —(CH$_2$)$_n$—NH$_2$ wherein n is an integer from 0 to 6, a straight or branched C$_{1-6}$ alkyl, a straight or branched C$_{2-6}$ alkenyl or a C$_{1-6}$ alkoxy.

10. The method of claim 9 wherein A is methyl, X is —NH$_2$ and Z is H.

11. The method of claim 9 wherein A is methyl, X is —NH$_2$ and Z is amino.

* * * * *

UNITED STATES PATENT AND TRADEMARK OFFICE
Certificate

Patent No. 5,808,068                                                 Patented: September 15, 1998

On petition requesting issuance of a certificate for correction of inventorship pursuant to 35 U.S.C. 256, it has been found that the above-identified patent, through error and without any deceptive intent, improperly sets forth the inventorship.

Accordingly, it is hereby certified that the correct inventorship of this patent is: David Callaway, Peter Ulrich, Senliang Pan, Michael Bukrinsky, Omar K. Haffar.

Signed and Sealed this Sixteenth Day of May, 2000.

JOSE' DEES
*Supervisory Patent Examiner*
Technology Center 1600
Art Unit 1616